(12) United States Patent
Liang

(10) Patent No.: US 7,244,865 B2
(45) Date of Patent: Jul. 17, 2007

(54) PROCESS FOR PREPARING BENZHYDRYLTHIOACETAMIDE

(75) Inventor: Sidney Liang, Olivette, MO (US)

(73) Assignee: Mallinckrodt Inc., Hazelwood, MO (US)

( * ) Notice: Subject to any disclaimer, the term of this patent is extended or adjusted under 35 U.S.C. 154(b) by 136 days.

(21) Appl. No.: 10/537,965

(22) PCT Filed: Feb. 23, 2004

(86) PCT No.: PCT/US2004/005265

§ 371 (c)(1), (2), (4) Date: Jun. 9, 2005

(87) PCT Pub. No.: WO2004/075841

PCT Pub. Date: Sep. 10, 2004

(65) Prior Publication Data

US 2006/0160903 A1 Jul. 20, 2006

Related U.S. Application Data

(60) Provisional application No. 60/449,629, filed on Feb. 24, 2003.

(51) Int. Cl.
C07C 233/00 (2006.01)
C07C 319/20 (2006.01)
(52) U.S. Cl. .................................................... 564/162
(58) Field of Classification Search ...................... None
See application file for complete search history.

(56) References Cited

U.S. PATENT DOCUMENTS

| 4,066,686 A | 1/1978 | Lafon |
| 4,098,824 A | 7/1978 | Lafon |
| 4,127,722 A | 11/1978 | Lafon |
| 4,177,290 A | 12/1979 | Lafon |
| 4,489,095 A | 12/1984 | Lafon |
| 4,713,246 A | 12/1987 | Begum et al. |
| 4,880,623 A | 11/1989 | Piergiorgio et al. |
| 4,895,726 A | 1/1990 | Curtet et al. |
| 4,927,855 A | 5/1990 | Lafon |
| 4,952,574 A | 8/1990 | Banitt |
| 5,021,242 A | 6/1991 | Römer et al. |
| 5,180,745 A | 1/1993 | Lafon |
| 5,202,129 A | 4/1993 | Samejima et al. |
| 5,391,576 A | 2/1995 | Lafon |
| 5,719,168 A | 2/1998 | Laurent |
| 5,932,707 A | 8/1999 | Archer et al. |
| 6,492,396 B2 | 12/2002 | Bacon et al. |
| 6,649,796 B2 | 11/2003 | Naddaka et al. |
| 6,670,358 B2 | 12/2003 | Bacon et al. |
| 6,849,120 B2 | 2/2005 | Singer et al. |
| 6,875,893 B2 | 4/2005 | Largeau et al. |
| 6,919,367 B2 | 7/2005 | Bacon et al. |
| 2002/0043207 A1 | 4/2002 | Singer et al. |
| 2002/0183552 A1 | 12/2002 | Naddaka et al. |
| 2004/0002547 A1 | 1/2004 | Largeau et al. |
| 2004/0102523 A1 | 5/2004 | Broquaire et al. |
| 2004/0106829 A1 | 6/2004 | Fornaroli et al. |
| 2005/0034652 A1 | 2/2005 | Ceausu et al. |

FOREIGN PATENT DOCUMENTS

| CN | 1432565 | 7/2003 |
| EP | 0097071 A1 | 12/1983 |
| EP | 233106 A1 | 1/1987 |
| EP | 0233106 B1 | 8/1987 |
| EP | 0283362 A1 | 9/1988 |
| EP | 1260501 A1 | 11/2002 |
| WO | WO 94/21371 | 9/1994 |
| WO | WO 02/10125 A1 | 2/2002 |
| WO | WO 02/30414 | 4/2002 |
| WO | WO 03/099774 | 12/2003 |
| WO | WO 2004/075841 A | 9/2004 |

*Primary Examiner*—Brian Davis
(74) *Attorney, Agent, or Firm*—Blackwell Sanders Peper Martin LLP; Ray Loyer; Sarah Vaz

(57) ABSTRACT

The present invention is directed to an improved process for preparing modafinil wherein benzhydrylthioacetamide is prepared in high yield and purity by the reaction of a haloacetamide with the reaction product of thiourea and benzhydrol in aqueous solution. The reaction employing the haloacetamide is conducted in a solvent comprising water and an organic solvent such as dimethylformamide having dissolved therein a basic salt such as potassium carbonate. The resulting benzhydrylthioacetamide can be oxidized to provide the pharmaceutical modafinil.

32 Claims, No Drawings

PROCESS FOR PREPARING BENZHYDRYLTHIOACETAMIDE

CROSS REFERENCE TO RELATED APPLICATIONS

This application is a national stage application of PCT/US2004/005265, filed Feb. 23, 2004, which claims the benefit of U.S. Provisional Application No. 60/449,629, filed Feb. 24, 2003.

This invention relates to an improved process for preparing modafinil wherein the intermediate, benzhydrylthioacetamide, is prepared in a reaction medium comprising an organic solvent and water having dissolved therein a basic salt. The amide thus produced is oxidized to provide benzhydrylsulphinylacetamide, commonly known as modafinil.

BACKGROUND OF THE INVENTION

Lafon disclosed modafinil and other similar compounds in U.S. Pat. No. 4,177,290 as having pharmaceutical activity on the central nervous system. In a typical prior art process, benhydrylthioacetic acid is halogenated with thionyl chloride. The chloride is then converted to the amide in methylene chloride with ammonia. The amide is then oxidized with hydrogen peroxide to provide benzhydrylsulphinylacetamide. Other derivatives of modafinil as well as methods of preparation and purification are disclosed in U.S. Pat. No. 4,127,722. However, the amide appears to be the compound of choice among the many derivatives now known.

Interest in the Lafon compounds has increased in recent years because these compounds have been discovered to have beneficial effects in the treatment of a wide variety of diseases in mammals including humans. Although first noted as a treatment for narcolepsy, more recent patents and technical publications have listed such compounds as beneficial in the treatment of Parkinson's disease, urinary incontinence, Alzheimer's disorder, ischemia and stroke. As the use of these compounds increased so has the demand for greater volumes while maintaining the highest state of purity and also avoiding process chemicals of high environmental risk.

Numerous substituted thioacetamides are disclosed in U.S. Pat. No. 6,492,396 to Bacon et al. In one syntheses scheme benzhydrol is converted to a benzhydrylthiol by reaction with thiourea that is then converted by hydrolysis to a thiouronium moiety. Subsequently, the thiouronium is converted to an acid with chloroacetic acid. The benzhydrylthioacetic acid is treated in various ways depending upon the desired derivative. To prepare the amide the acid is reacted with ammonia or an appropriate amine in an organic solvent such as tetrahydrofuran or methylene chloride. Other thioacetamide derivatives are obtained by employing N-methylmorpholine and a thioacetic acid in dimethylformamide (DMF).

A procedure for the preparation of an acetamide intermediate for the production of modafinil is disclosed in published U.S. application Ser. No. 2002/0183552. According to this application a three-step procedure for preparing modafinil is disclosed starting with benzhydrol (diphenylmethanol) that is employed to prepare the benzhydrylthiocarboxamidine salt by reaction with thiourea in hydrogen bromide. The bromide salt is then reacted with chloroacetamide in aqueous sodium hydroxide to produce diphenylmethylthioacetamide. The acetamide may then be oxidized by conventional means to produce modafinil. Typically, the oxidation is provided by a reaction with hydrogen peroxide in glacial acetic acid.

Because of the growing demand for large quantities of modafinil in a highly pure state there is needed a process for preparing the product efficiently without need for undesirable starting materials or by-products. In particular the production of the acetamide intermediate is particularly in need of improvement although given some degree of attention in the art as indicated above.

SUMMARY OF THE INVENTION

In accordance with this invention there is provided a novel process for the preparation of benzhydrylthioacetamide by the reaction of a haloacetamide with the reaction product of thiourea and benzhydrol. The improved process is conducted in a solvent comprising water, having dissolved therein a basic salt and a water miscible organic solvent. The resulting benzhydrylthioacetamide is provided in high yield and purity and can be oxidized to provide the pharmaceutical modafinil.

The process of this invention provides improved yield and purity over known processes. The water miscible organic solvent provides the dual function of providing a solvent for the starting organic material while also providing a convenient reaction medium allowing low temperature reactions to take place.

DETAILED DESCRIPTION OF THE INVENTION

The pharmaceutical modafinil is conveniently prepared in three steps including the novel step of this invention wherein DMF and a basic salt is employed. First, benzhydrol 1 is reacted with thiourea 2 to provide a reaction product that is sometimes termed the benzhydrylthiocarboxamidine salt 3. This reaction is carried out in water in the presence of hydrogen bromide at a temperature of about 90° C. A solid benzhydrylthiocarboxamidine bromide salt precipitates. The reaction may be described structurally as follows:

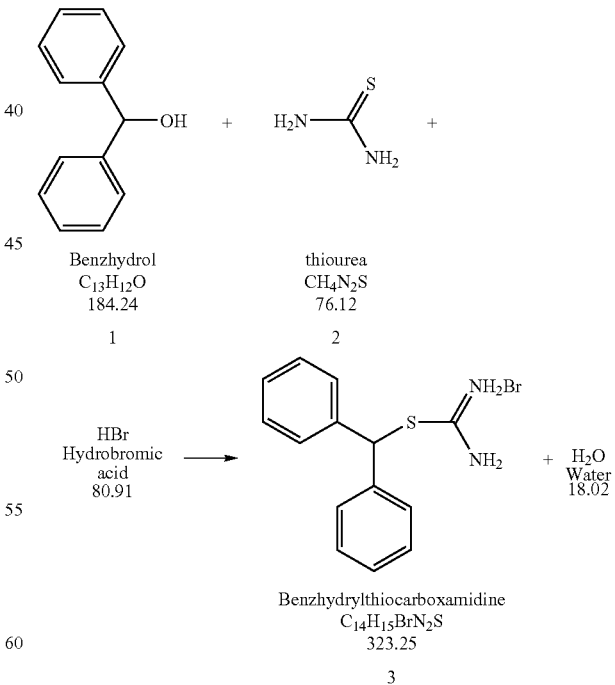

In the second step, the benzhydrylthiocarboxamidine bromide 3 salt is washed with water then placed in a reaction vessel together with chloroacetamide 4, a basic salt, DMF, and water. This mixture is stirred to dissolve the bromide salt and to allow it to react at or near room temperature.

Although the reaction is described with respect to the bromide salt, any other suitable salt may be employed. When the reaction is completed the reaction mixture is diluted with water and a solid precipitate is separated. When washed with water, benzhydrylthioacetamide 5 is obtained in high yield and purity. The reaction may be described structurally as follows:

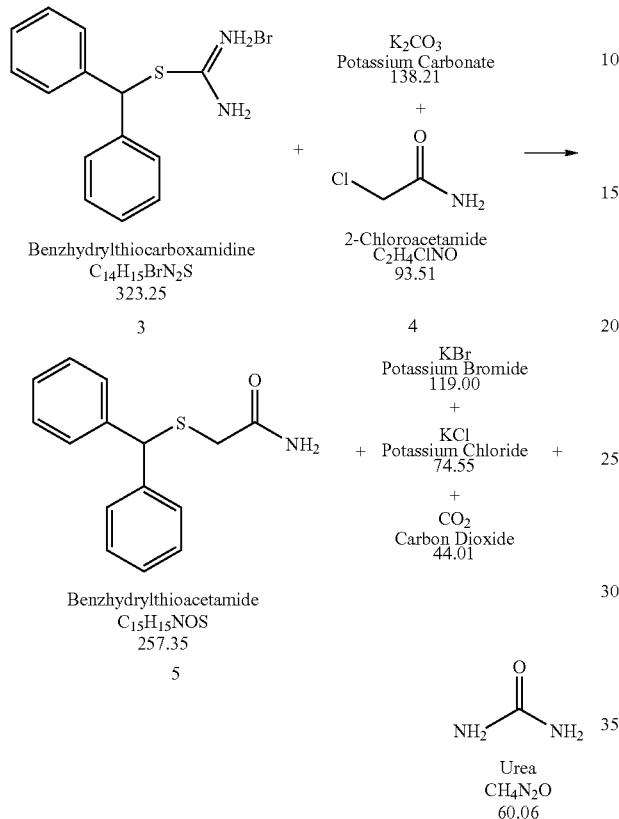

In the third step of the procedure to obtain modafinil in accordance with this invention benzhydrylthioacetamide 5 is dissolved in acetic acid and hydrogen peroxide is slowly charged to the solution while cooling to control the exothermic reaction. Typically the temperature is maintained below 22° C. to prevent undesired side reactions. After the reaction is completed, the product is isolated by diluting the reaction mixture with water and separating the precipitate to obtain a crude racemic benzhydrylsulphinylacetamide 6 (modafinil). The crude product is typically refined by recrystallization in a solvent or a mixture of solvents including chloroform to obtain highly pure pharmaceutical grade modafinil. The reaction may be described structurally as follows:

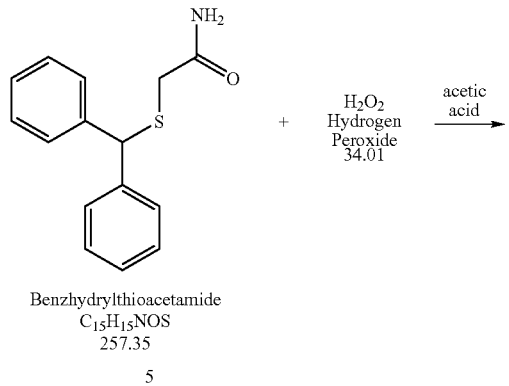

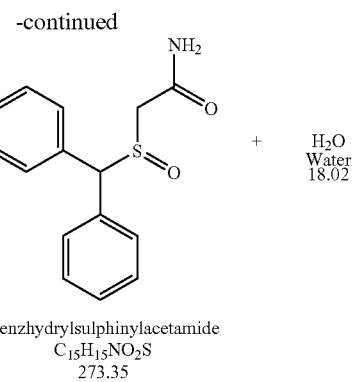

The term "alkali metal" encompasses lithium, sodium, potassium, cesium and rubidium; and the term "alkaline earth metal" includes beryllium, magnesium, calcium, strontium and barium. Typically, the preferred alkali metals are sodium and potassium while the preferred alkaline earth metal salts are calcium and magnesium.

On small-scale reactions, the use of a water-soluble organic solvent and alkali metal carbonate produced the expected product in very high purity. Unfortunately, upon increasing the scale, excessive amounts of byproducts were produced as well as extreme discoloration of the product.

In an attempt to determine which possible initial impurities could cause the large-scale deviation, it was found that excess amounts of un-reacted thiourea from previous reactions impaired the desired reaction path. It was also discovered that the minor presence of water had no detrimental effect on the reaction. In trying to assess the maximum limit of the water impurity, surprisingly it was found that water had an advantageous effect on the desired reaction path. Water prevented a number of byproducts from being formed while still allowing the desired reaction to proceed. Continued experiments using a water miscible organic solvent and water with a basic salt demonstrated a very efficient reaction at room temperature with excellent yields. It has been found that the ratio of water miscible organic solvent to water in the reaction medium can be in a wide range. Typically the volume ratio of water miscible organic solvent/water is in the range of from about 9/1 to about 1/9 and preferably from about 2/1 to about 1/1. The most preferred range is about 3/2.

Any suitable water miscible organic solvents can be employed in the process of this invention. The water miscible organic solvent must have some degree of solvating power with respect to the organic starting material benzhydrylthiocaboxamidine salt. Typically, such solvents include acetone and lower alkanols such as methanol, ethanol, butanol, sec-butyl alcohol and tert-butyl alcohol. However, it has been found that dimethylformamide (DMF) is particularly useful as well as other water miscible amides.

The process of this invention, employing a water miscible organic solvent/water reaction medium containing a basic salt, can be run at room temperature and produces isolated yields in the range of about 97% (based upon HPLC analysis) with the amount of impurities at less than 1%. Such results represent significant yield improvements as well as a more efficient process compared to all other known methods. This process eliminates a process step and the use of thionyl chloride and benzene in comparison to the '290 patent. The process of this invention also eliminates the use of high temperatures, corrosive solutions, and byproducts, while still producing higher yields with very low impurities compared to the prior art processes such as those that employ sodium hydroxide with haloacetamide in the above described published application.

Any number of basic salts can be employed in the process of this invention. Salts may be employed that may only be slightly soluble in water. However, the presence of the salt in the reaction medium remains effective to promote the reaction in the particulate form. Thus the term "water soluble" as employed herein includes material only slightly soluble in water. In particular, it is preferred to employ ammonium, alkali metal salts or alkaline earth metal salts. In particular, the sodium salt is preferred and the potassium salt is even more preferred. The anion of the salt is typically a sulfate, sulfide, phosphate, bicarbonate, nitrate, phosphonate, phosphinate and preferably a carbonate. Typical salts included in the above description of water soluble salts are sodium sulfate, calcium sulfate, magnesium sulfate, sodium sulfide, magnesium sulfide, calcium sulfide, sodium phosphate, magnesium phosphate, calcium phosphate, potassium phosphate, sodium bicarbonate, calcium bicarbonate, magnesium bicarbonate, sodium nitrate, calcium nitrate, magnesium nitrate, sodium phosphonate, potassium phosphonate, magnesium phosphonate, calcium phophonate, sodium phosphinate, potassium phosphinate, calcium phosphinate, magnesium phosphinate, potassium sulfate, potassium sulfide, potassium bicarbonate, potassium nitrate, potassium tripolyphosphate, sodium tripolyphosphate, sodium thiophosphate, potassium citrate, tetrapotassium pyrophosphate, ammonium phosphate, ammonium chloride, ammonium sulfate, ammonium bicarbonate, ammonium phosphinate, ammonium phosphonate and the like. Potassium carbonate is preferred because it is readily soluble in water.

The process of this invention has been found to be particularly advantageous over the prior art sodium hydroxide process. Said prior art process requires higher temperatures to help increase the yields since lower temperatures tend to produce significant amounts of impurities. A milder basic solution was thought to be sufficient enough to promote the reaction and at lower temperature conditions. Water and potassium carbonate were initially used, but byproducts were still produced. In a preferred embodiment, a mixture of DMF and potassium carbonate solution was employed to help dissolve the starting reagent and promote a more stable pH during the reaction. The amount of basic salt, by weight of the total the starting reagent benzhydrylthiocarboxamidine bromide salt employed in the process of this invention, is typically in the range of from about 41% to about 200% and preferably in the range of from about 82% to about 110% and most preferably in the range of from about 95% to about 105%.

In another aspect of this invention is the clean up of the final product, modafinil. It has been found that the final product was best purified by mixing it with chloroform. The preferred method is to then refluxing the mixture for a short period of time. The refluxed mixture is then cooled to a relatively low temperature, filtered and washed to provide a highly pure modafinil product. The use of methanol and/or methanol:/water solvent as disclosed in the original '290 patent to purify the modafinil was found to be inadequate or inefficient in obtaining pharmaceutically pure modafinil. Similar alcohol solvents such as ethanol and propanol also gave similar results wherein several impurities were significantly greater than 0.1%. Modafinil was only mildly soluble, at best, in alcoholic solvents even at reflux temperatures. Many impurities were also very insoluble in alcoholic solvents and were thus retained in modafinil. In many cases 1 g of crude modafinil required a minimum of 8 ml of methanol to be completely dissolved at reflux temperature. When filtered at room temperature, many impurities were only moderately reduced.

It also been found that excellent purification of modafinil can be achieved by mixing the crude modafinil product with a halo-organic solvent such as dichloromethane, dichloroethane and preferably chloroform. Chloroform was initially believed to be a better solvent for the clean-up procedure because it was slightly acidic in comparison to alcohols. Surprisingly, modafinil was also extremely insoluble in chloroform, but fortunately, the impurities were very soluble in chloroform. Major impurities in the crude modafinil product include the modafinil acid, modafinil sulfone acid, modafinil sulfone and unreacted starting material, benzhydrylthioacetamide. Crude modafinil was initially mixed with chloroform in 1 g crude to 4 ml chloroform. It has been found that the major impurities are substantially removed by the chloroform washing.

In a preferred embodiment a low boiling aliphatic solvent, preferably heptane can be added in a ratio of about 2 ml of solvent to about 1 g crude to help reduce the viscosity of the slurry. To address the problem of the viscous slurry, heptane can be charged first to the crude. Chloroform is then added to the stirred mixture slowly. A mild slurry, results. Heating the slurry to reflux further alleviates the viscosity to a simple solid/liquid mixture even when it was cooled to 5° C. allowing easy filtering with high yields. The slurry would become less viscous only upon heating to reflux for about 30 minutes. Even though the modafinil never completely dissolves in the solvent mixture, the cleaning procedure is effective. The solvent mixture is then cooled to about 5° C. allowing the modafinil to precipitate fully after which it can be filtered to obtain 92% to 97% recovery yield with ~99.8% purity by weight (HPLC analysis), respectively. In this preferred embodiment any suitable low boiling aliphatic solvent such as pentane, hexane, heptane, or octane may be employed The following examples are intended to illustrate the present invention and are not to limit the claims in any manner. All of the percentages are by weight unless otherwise indicated.

PREFERRED EMBODIMENTS OF THE INVENTION

EXAMPLE 1

Preparation of Benzhydrylthiocarboxamidine Bromide Salt.

To a reaction vessel there was charged 82.63 g of thiourea, 150 ml of HBr (48%) and 200 ml of water. Then, 100 g of benzhydrol were charged to the mixture in the reaction vessel. The reaction mixture was then refluxed at 90° C. for 5 hr. The reaction mixture was then cooled to room temperature and 100 ml of additional water were added to the mixture followed by filtration. The crude solid residue was rinsed with 75 ml and air dried to provide approximately 90% (molar) yield at greater than 95% purity.

EXAMPLE 2

Preparation of Benzhydrylthioacetamide (a)

To a 500 ml. round bottom flask there were added 10 g of benzhydrylthiocarboxamidine bromide from Example 1, 3.46 g of chloroacetamide, 10.7 g of potassium carbonate and 60 ml of DMF. This mixture was stirred and 40 ml of water was added. An exothermic reaction occurred and the temperature rose to 53° C. The reaction mixture was cooled to room temperature with continued stirring at room temperature over night. The resulting solution exhibited a slight, minimal yellow tinge. Liquid chromatography indicated very little by product and stirring continued over night again. The reaction mixture was then cooled to 15° C. and slowly diluted with 200 ml water to maintain the temperature below 22° C. A precipitate formed and the reaction mixture was filtered to obtain 7.6 g of product Analysis by HPLC indicated the presence of benzhydrylthioacetamide in 98% purity.

EXAMPLE 3

Preparation of Benzhydrylthioacetamide (b)

The procedure of Example 2 was repeated except the amount of reactants was increased and the temperature more carefully controlled. To the round bottom flask were added 20 g of benzhydrylthiocarboxamidine bromide, 7 g of chloroacetamide, 21.5 g of potassium carbonate, and 100 ml of DMF. The reaction mixture was cooled to 10° C. in an ice bath and 40 g of water was slowly added so as to maintain the temperature of the reaction mixture below 22° C. The reaction mixture was stirred for 48 hr at room temperature. Then the reaction mixture was cooled to 10° C. and then 300 ml of water were added to the reaction mixture while maintaining the mixture below 22° C. An exothermic condition was observed during the water addition. The reaction mixture was then filtered and the solid washed with 100 ml of water to obtain 15.3 g of product. Analysis by HPLC indicated the product was 98% pure.

EXAMPLE 4

Preparation of Benzhydrylthioacetamide (c)

To a 2L three-necked flask there were added 197 g of crude benzhydrylthiocarboxamidine bromide, (theoretical maximum 175 g), 61 g of chloroacetamide, 187 g of potassium chloride and 400 ml of DMF. The reaction mixture was cooled to a range of from 10° C. to 15° C. Then, 175 ml of water were charged to the reaction vessel while maintaining the temperature of the reaction mixture below 20° C. The final temperature when finishing the water addition reached 12° C. The water bath was removed and the reaction mixture stirred over night at room temperature. Then the reaction mixture was cooled to 5° C. and 1L of water was slowly charged to the reaction mixture. The reaction mixture was filtered to collect a 135 g of precipitate (dry weight). Analysis by HPLC indicated that the product was 99% pure.

EXAMPLE 5

Preparation of Benzhydrylsulphinylacetamide

To a 500 ml three-necked round bottom flask was charged 50 grams of benzhydrylthioacetamide and 100 ml of acetic acid. The mixture was stirred until all solids were dissolved and then the reaction mixture was cooled to 15° C. There were then slowly added to the reaction mixture 25 ml of hydrogen peroxide solution (30%) in step-wise fashion (5-10 ml portions) while maintaining the temperature of the reaction mixture below 20° C. The reaction mixture was then stirred at room temperature (20° C.) or until the amide disappeared. There was then added 500 ml of water to the reaction mixture thereby precipitating the product. The reaction mixture was cooled to 15° C. and filtered. The crude solid product was then rinsed with 50 ml of water. The product was then purified by combining it with heptane (3.5 ml/1 g crude) and then chloroform (7 ml/1 g of crude). The mixture was refluxed for 30 min. at a temperature of 70-75° C. The solution was slowly cooled to 10° C. with stirring and the solid precipitate then filtered and oven dried. The yield was 85% (molar) and the purity was 99.8%.

Although the invention has been described in terms of specific embodiments which are set forth in considerable detail, it should be understood that this description is by way of illustration only and that the invention is not necessarily limited thereto since alternative embodiments and operating techniques will become apparent to those skilled in the art in view of the disclosure. Accordingly, modifications are contemplated which can be made without departing from the spirit of the described invention.

The invention claimed is:

1. A process for the preparing of benzhydrylthioacetamide comprising reacting benzhydrylthiocarboxamidine salt with haloacetamide in a reaction medium comprising water, a water miscible organic solvent and a water soluble basic salt selected from the group consisting of alkali metal and alkaline earth metal sulfates, sulfides, phosphates, carbonates, bicarbonates, nitrates, phosphates and phosphinates.

2. The process of claim 1 wherein the haloacetamide is chloroacetamide.

3. The process of claim 1 wherein the basic salt is a potassium salt.

4. The process of claim 3 wherein the basic salt is a potassium carbonate salt.

5. The process of claim 1 wherein the basic salt is present in a weight ratio to benzhydrylthiocarboxamidine salt of from about 41 to about 200.

6. The process of claim 5 wherein the basic salt is present in the weight ratio of from about 82 to about 110.

7. The process of claim 5 wherein the basic salt is present in the weight ratio of about 105.

8. The process of claim 1 wherein the volume ratio of water miscible organic solvent to water is in the range of from about 9/1 to 1/9.

9. The process of claim 8 wherein the volume ratio of water miscible organic solvent to water is in the range of from about 2/1 to 1/1.

10. The process of claim 8 wherein the volume ratio of water miscible organic solvent to water is about 3/2.

11. The process of claim 1 wherein the water miscible organic solvent is selected from the group consisting of lower alkanols, acetone and dimethylformamide.

12. The process of claim 11 wherein the lower alkanol is selected from the group consisting of methanol, ethanol, butanol, sec-butyl alcohol, and tert-butyl alcohol.

13. In a process for preparing modafinil comprising the following steps:
reacting benzhydrol with thiourea in the presence of hydrogen bromide to provide benzhydrylthiocarboxamidine bromide;
reacting haloacetamide with the product of step a) to provide benzhydrylthioacetamide;
oxidizing the product of step b) to obtain benzhydrylsulphinylacetamide; and
the improvement which comprises conducting the reaction of step b) in a solvent comprising a water miscible organic solvent, and water in the presence of a basic salt selected from the group consisting of alkali metal and alkaline earth metal sulfates, sulfides, phosphates, carbonates, bicarbonates, nitrates, phosphates and phosphinates.

14. The process of claim 13 wherein the haloacetamide is chloroacetamide.

15. The process of claim 13 wherein the basic salt is a potassium salt.

16. The process of claim 15 wherein the basic salt is a potassium carbonate salt.

17. The process of claim 13 wherein the basic salt is present in a weight ratio to benzhydrylthiocarboxamidine salt of from about 41 to about 200.

18. The process of claim 17 wherein the basic salt is present in the weight ratio of from about 82 to about 110.

19. The process of claim 18 wherein the basic salt is present in the weight ratio of about 105.

20. The process of claim 13 wherein the volume ratio of water miscible organic solvent to water is in the range of from about 9/1 to 1/9.

21. The process of claim 20 wherein the volume ratio of water miscible organic solvent to water is in the range of from about 2/1 to 1/1.

22. The process of claim 20 wherein the volume ratio of water miscible organic solvent to water is about 3/2.

23. The process of claim 13 wherein the water miscible organic solvent is selected from the group consisting of lower alkanols, acetone and dimethylformamide.

24. A process for the purification of modafinil which comprises contacting the crude modafinil with a halo-organic solvent and then separating the modafinil from the solvent.

25. The process of claim 24 wherein the temperature of the mixture of modafinil and halo-organic solvent is raised to a reflux temperature.

26. The process of claim 25 wherein the reflux temperature is maintained for about 30 minutes.

27. The process of claim 24 wherein the halo-organic solvent is selected from the group consisting of chloroform, dichloromethane, and dichloroethane.

28. The process of claim 24 further including the step of adding an aliphatic solvent to the mixture.

29. The process of claim 28 wherein an aliphatic solvent is added to modafinil prior to contacting the modafinil with the halo-organic solvent and the temperature of the mixture is raised to the reflux temperature.

30. The process of claim 29 wherein the reflux temperature is maintained for about 30 minutes.

31. The process of claim 29 wherein the aliphatic solvent is selected from the group consisting of pentane, hexane, heptane and octane.

32. The process of claim 28 wherein the halo-organic solvent is chloroform and the aliphatic solvent is heptane.

* * * * *